(12) United States Patent
Wang

(10) Patent No.: US 7,364,560 B2
(45) Date of Patent: Apr. 29, 2008

(54) AMBULATORY HIP FIXATION-TRACTION SPLINT FRAME

(76) Inventor: Ming-Hua Wang, Room 601, No. 21, Dong Bao Road, Hangzhou, Zhejiang, PRC, 310016 (CN)

( * ) Notice: Subject to any disclaimer, the term of this patent is extended or adjusted under 35 U.S.C. 154(b) by 808 days.

(21) Appl. No.: 10/785,897

(22) Filed: Feb. 23, 2004

(65) Prior Publication Data
US 2004/0167451 A1 Aug. 26, 2004

Related U.S. Application Data

(63) Continuation-in-part of application No. 10/359,670, filed on Feb. 7, 2003, now Pat. No. 7,087,030.

(51) Int. Cl.
*A61F 5/00* (2006.01)
(52) U.S. Cl. .............................. 602/23; 602/26; 135/68
(58) Field of Classification Search ............... 602/5.16, 602/19, 23, 26, 5, 16; 135/68, 69, 74–76
See application file for complete search history.

(56) References Cited

U.S. PATENT DOCUMENTS 2,189,429 A * 2/1940 Lundquist .................... 135/68
2,778,370 A * 1/1957 Chamblee .................... 135/68
6,015,395 A * 1/2000 Kautzky ...................... 602/19

* cited by examiner

*Primary Examiner*—Michael A. Brown
(74) *Attorney, Agent, or Firm*—Raymond Y. Chan; David and Raymond Patent Firm

(57) ABSTRACT

An ambulatory hip fixation-traction splint frame includes a supporting frame having an upper end arranged for positioning below an armpit of a treated patient and a lower end arranged for positioning below a hip portion of the treated patient, and a side splint assembly for supporting a side body of the treated patient. The side splint assembly includes a flexible guiding frame having first and second ends, and a curved guiding surface, having a predetermined curvature, defining between the first and second ends for biasing against the side body of the treated patient, and two coupling joints adjustably mounted on the supporting frame to connect with the first and second ends of the guiding frame respectively so as to retain the curvature of the guiding surface of the guiding frame for fitting on the side body of the treated patient.

23 Claims, 8 Drawing Sheets

AMBULATORY HIP FIXATION-TRACTION SPLINT FRAME

CROSS-REFERENCE OF RELATED APPLICATION

This is a Continuation-In-Part application of a non-provisional application having an application Ser. No. 10/359,670 and a filing date of Feb. 7, 2003 now U.S. Pat. No. 7,087,030.

BACKGROUND OF THE PRESENT INVENTION

1. Field of Invention

The present invention relates to a splint, and more particularly to an ambulatory hip fixation-traction splint frame which is capable of applying to a patient with hip fracture, hip disease or other disorders to not only keep the hip of the patient in suitable fixation position but also create ambulatory traction, assist the patient out of the limitation of the bed, have a suitable movement and a convenient nursing, so as to enhance the recovery of the injury area with less complication for old patients especially.

2. Description of Related Arts

According to the National Institute of Arthritis and Musculoskeletal and Skin Diseases (NIAMS), Osteoporosis is one of the major health risks for tens of millions of Americans. Every year osteoporosis is responsible for more than 1.5 million fractures, which include 300,000 hip fractures, approximately 700,000 vertebral fractures, 250,000 wrist fractures, and more than 300,000 other fractures. Patients with osteoporosis may have fractures induced from normal movement action, such as lifting, bending, or accidental falling in different parts of their bodies such as the hip area. Therefore, there is a strong demand for treatment methods for osteoporosis. And in fact, together with those having bones fractures or the like by accident, there is a great number of patients suffering from bones diseases or related problems such as broken bones, bones fractures, hip disorders or other disorders.

Immobilization is one of the most popular and efficient treatment methods for bones diseases or support system related problems, such as bone fractures, broken legs, dislocations, or other bone and joint disorders. Orthoses, such as braces, splints or casts, are widely developed and used for external fixation. Existing methods of immobilization by orthoses as external fixation for areas such as neck, elbow, wrist, knee, or ankle are proved to be very effective and efficient.

Commonly, the immobilization methods could be categorized into three forms: splint immobilization, plaster splint immobilization and small splint immobilization.

Splint immobilization refers to the fixation by a plank, bamboo or sheet metal splint. The drawbacks of this method are inferior fixation, and failure of functional fixation. As a result, this method has been eliminated in clinical practices. Right now, it is merely regarded as a first aid treatment for temporary fixation.

Thanks to its accuracy and application of X-ray technology, fracture and reduction can be seen, plaster splint immobilization, together with its accompanying traction process, has been widely used in practices. This method is based on fracture reduction and has been proved high effectiveness. It is known that plaster immobilization process comprises three characteristics.

(a) Reduction process is usually one-time accomplished by doctor. Here, reduction includes close reduction or open reduction, functional reduction or anatomical reduction.

(b) Immobilization is long range three-point fixation and long time static fixation, plaster shoulder be employed until the full recovery of the fracture. Here, the fixation is external fixation.

(c) Rehabilitation (functional exercising) and post-treatment are concerned so as to recover the normal joint motion and human ability.

Small splint immobilization is purposely devised to satisfy some extents of body movement thereby improving the functional recovery of patients. However, this method needs 4-5 pieces of small splints, willows, and clothed preplasticizing materials working together. Obviously, these stuffs are inconvenient and complicated. Meanwhile, several cords have to be employed for binding the small splints with wounded body thus causing doctor to adjust the cords-binding tightness from time to time to prevent the cord distortion, to match the subsidence of the edema.

Yet there is still no effective or efficient immobilization method for hip fracture or its vicinities. Among existing methods of immobilization by external fixation for hip or thigh diseases, spica cast or splints immobilization for fixing the fracture or injury parts in position are commonly used. However, either a spica cast or a traditional splint is not an ideal method for immobilization, especially for the old. These two common methods, a spica cast or a traditional splint, make patient on bed with extensive fixation for a long time, pose high risk of complications or side effects, such as pressure sores or pneumonia, as well as result to high mortality. In case if too much space is left for allowing movement, these two methods are inadequate for fixation and immobilization.

For some patients, traditional traction can be achieved for the reduction and fixation of unstable fracture. Unfortunately, traditional traction including both skeletal traction and skin traction must be applied on a lying surface such as a bed and balanced by cords with pulleys and weights. Therefore, patients with hip fractures or bone diseases must be laid on a bed if traditional traction is applied for assisting movement. However, since patients with hip fractures or bone diseases usually require a long period of time for recovery, and traditional traction cannot assist patients to have movement out of the bed, patients will ultimately required to lie on the bed for a long period of time. If suitable movement or exercise cannot be accompanied as a recovery treatment, many problems such as pressure sores, pneumonia, and deterioration of healthy organs of the patient may gradually appear and hence adversely affect the life quality and health of the patient. Meanwhile, traction also leads to 50% coax vara, and high mortality.

Meanwhile, small splint immobilization is not suitable for hip portion fracture. For many years, many other methods and attempts have been devoted to treat hip fracture or illness of head of femur. However, the results have been disappointing. For instance, internal fixation by operation risks too much patients' life and is responsible for an enlarged wound area. Extra fixation is required for osteoporosis patients, almost one third of patients with neck fracture suffered nonunion afflictions after the operation, and patients face a second operation to remove affixed means. This method is conflicting with the ultimate surgery goal: micro wound and non-wound.

Similarly, another treating innovation for hip fracture, artificial joint, has a lot of problems, due to its wounding risks, high costs, early and late operation complications.

More importantly, foreign body is not favored for the factors of the human body, such as modulus of elasticity, material rejection or irritability, and uneasy abrasiveness. Conclusively, a better local fixation and bone healing will be able to improve treating effects for hip fracture and win overall acclaims in the arts.

Suitable traction or guidance is effective, useful or required for fixation and recovery. Currently, many methods or equipment are developed, but the patient is required to lie on a bed all the time. In addition, traction of lower extremity is a preferred assistant treatment options before and after the operation.

Accordingly, a walking stick is widely used in different situations for providing support to the old, to hikers and to the weak, and walking cast is used for those with broken or fracture bones such as broken ankles, broken fibula, broken shinbone, broken kneecap (patella). When the walking stick or the walking cast is used for providing support to a patient or for orthopedic purposes, it is particularly important that the walking stick or the walking cast is capable of providing a rigid, yet protective and flexible support according to the body movement as being a protective and movable support so as to lessen the load or stress of the patient, and to prevent the collapse of the walking stick and worsen a broken or weakened part of the patient. However, in the case of hip fractures or hip diseases, a walking stick is far from adequate for protection, assisting movement or traction.

For example, if a patient having a hip fracture uses the walking stick for standing or even walking, he will probably fall down and worsen his situation. Hip fracture will lead to chain collapses of support system right from the hip, even though his legs have no problems. If he tries to stand or walk with a stick, great pressure or too much pressure will be applied on his hip, be focused on a weaken part, i.e., the fracture part. This kind of pressure will cause displacement or distortion of his hip, spreading of the fracture area, or even breakage the fracture area. Therefore, existing walking stick is not suitable for assisting movement by traction. The support of a walking stick is not concrete and adequate. If the pressure or stress, which is originally concentrated on the hip especially the hip fracture area, could be spread to, or shared by other parts of the body and hence reduced in the hip area, the possibility of standing or even walking will be highly increased and become possible.

There are also different methods for aiding movement for the injured person with leg traction. For example, a hanging weight support associated with a pulley and a cord, and a bed comprising a rear part which may be uplifted are used together, so that the patient may use his own body weight in aiding movement by traction, such as lifting his lower body or stretching himself, or supporting and moving himself for gaining a certain degree of exercise or moving ability. However, the injured person is still required to lie on his own bed.

There are many disadvantages in lying on a bed. Recovery of our skeleton or support system usually takes time, and it may take several weeks, months or even years. If a patient is required to lie on a bed for a long time, his respiratory system, blood circulation system, digestive system or other healthy parts of support system will be adversely affected or deteriorated due to lack of movement or exercise. In the worst case, certain diseases or symptoms such as inflammation, swollen blood vessels, or even serious complications such as deadly pneumonia may be induced. These diseases are particularly harmful and disastrous to the old and/or the weak patient.

Furthermore, recovery always relies heavily on the emotional stability and status of the patient. If movement ability of the patient is limited or prohibited, serious emotional instability may be caused. When the patient feels that he needs to depend on others or he could not take care himself, he may be upset and unhappy. And this kind of emotional instability will be unavoidably happened from time to time when the movement ability of the injured is lost or limited. Therefore, any equipment which can aid in movement or allowing the patient to have certain degree of movement will greatly promote the recovery of the injured person.

Therefore, there is a need to have a kind of ambulatory hip fixation-traction splint frame, making hip fixation but aiding body movement, and that the splint is capable of providing a rigid, yet protective and flexible support while the move of the injured person, so as to prevent or lessen pressure or force applied on the hip fracture.

SUMMARY OF THE PRESENT INVENTION

A main object of the present invention is to provide an ambulatory hip fixation-traction splint frame which is capable of applying to a patient with hip fracture, hip disease or other disorders to not only keep the fracture area of the patient in fixation position but also assist the patient to have a suitable movement so as to enhance the recovery of the fracture area.

Another object of the present invention is to provide an ambulatory hip fixation-traction splint frame which is capable of applying to a patient with hip fracture, hip disease or other disorders to not only keep the fracture area of the patient in fixation position but also assist the patient to have a traction unlimited out of the bed, so as to permit a suitable body movement or ambulation, and to enhance the chance of recovery of the hip fracture.

Another object of the present invention is to provide an ambulatory hip fixation-traction splint frame, wherein a curvature of a guiding surface of a side splint assembly can be selectively adjusted to fittedly fix to the patient so as to retain the fracture area of the patient in suitable functional position.

Another object of the present invention is to provide an ambulatory hip fixation-traction splint frame which comprises a supporting frame adapted for distributing a weight of the patient while the fracture area of the patient is retained in the fixation position, so that the patient is allowed to have the body movement without pressurizing on the fracture area thereof and imposing harm.

Another object of the present invention is to provide an ambulatory hip fixation-traction splint frame, wherein the guiding frame is capable of providing a retraction force against the weight of the patient so as to minimize the weight of the patient pressured on the fraction area thereof and enhance the mobility of the patient.

Another object of the present invention is to provide an ambulatory hip fixation-traction splint frame, wherein a footstep is adjustably mounted on the supporting frame for tracting the patient's leg, so as to further minimize the weight of the patient pressured on the fraction area thereof through the patient, especially during walking.

Another object of the present invention is to provide an ambulatory hip fixation-traction splint frame, wherein a footstep is adjustably mounted on the supporting frame, fitting to the hip rotation through the foot, for support so as to further maintain the stability of the fracture area, especially during standing or walking.

Another object of the present invention is to provide an ambulatory hip fixation-traction splint frame which comprises a front splint assembly, such as a front arc guiding frame, adapted for fixing on a front side of the patient to limit the forward bending movement of the body of the patient so as to further retain the fracture area of the patient in the fixation position during movement.

Another object of the present invention is to provide an ambulatory hip fixation-traction splint frame, wherein no expensive or complicated structure is required to employ in the present invention in order to achieve the above mentioned objects. Therefore, the present invention successfully provides an economic and efficient joint system solution for not only providing a substantial support to retain the fracture area of the patient in the fixation position but also allowing the patient to have a suitable movement or exercise to be accompanied as a recovery treatment.

Accordingly, in order to accomplish the above objects, the present invention provides an ambulatory hip fixation-traction splint frame for a treated patient, comprising:

a supporting frame having an upper end arranged for positioning below an armpit of the treated patient and a lower end arranged for positioning below a hip portion of the treated patient; and a side splint assembly, comprising:

a flexible guiding frame having first and second end portions, and a curved guiding surface, having a predetermined curvature, defining between the first and second ends for biasing against a side body of the treated patient; and two coupling joints adjustably mounted on the supporting frame to connect with the first and second end portions of the guiding frame respectively so as to retain the curvature of the guiding surface of the guiding frame for fitting on the side body of the treated patient.

These and other objectives, features, and advantages of the present invention will become apparent from the following detailed description, the accompanying drawings, and the appended claims.

DETAILED DESCRIPTION OF THE PREFERRED EMBODIMENT

Figure 1:
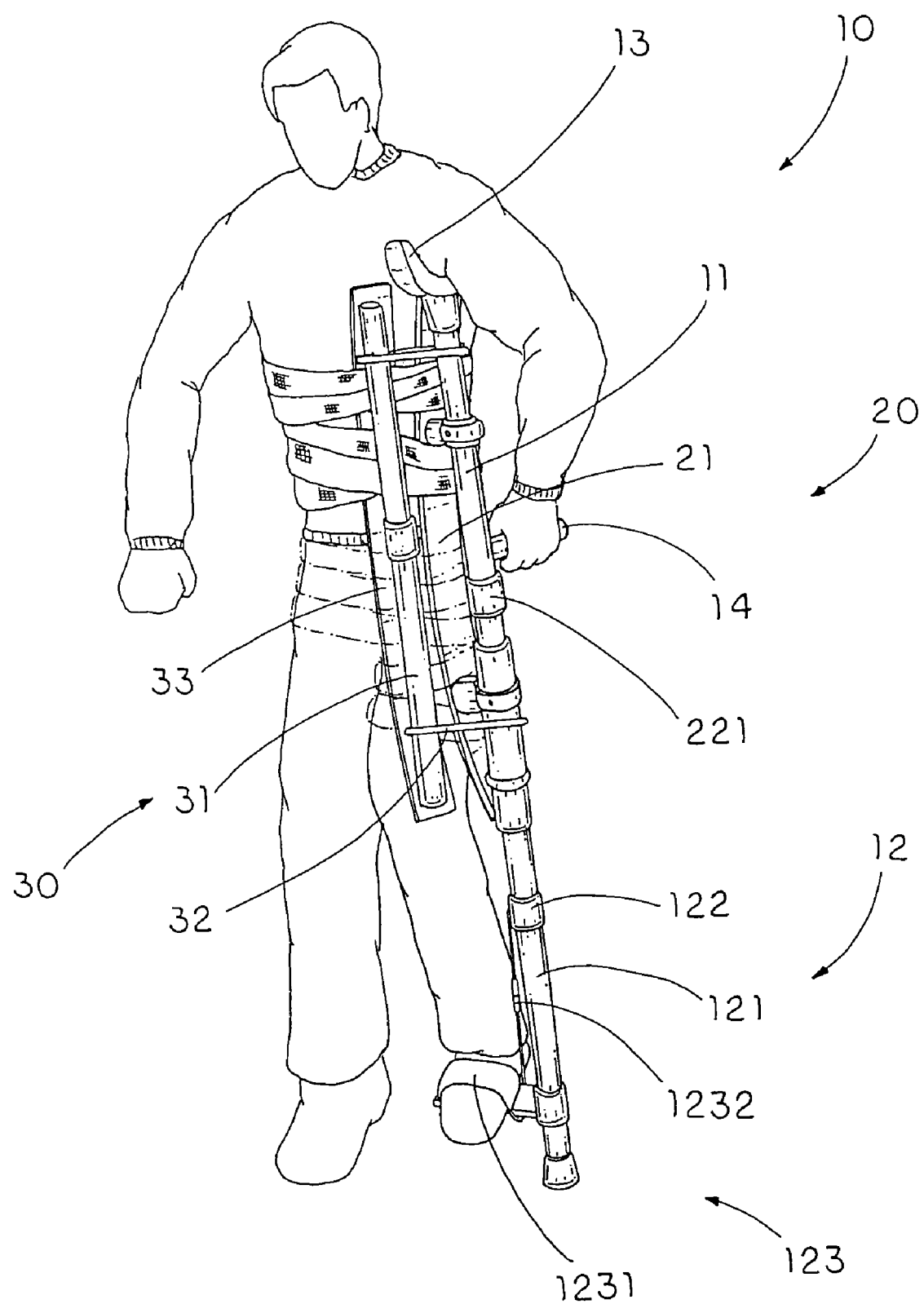
FIG. 1 is a perspective view of an ambulatory hip fixation-traction splint frame according to a first preferred embodiment of the present invention.
Figure 2:
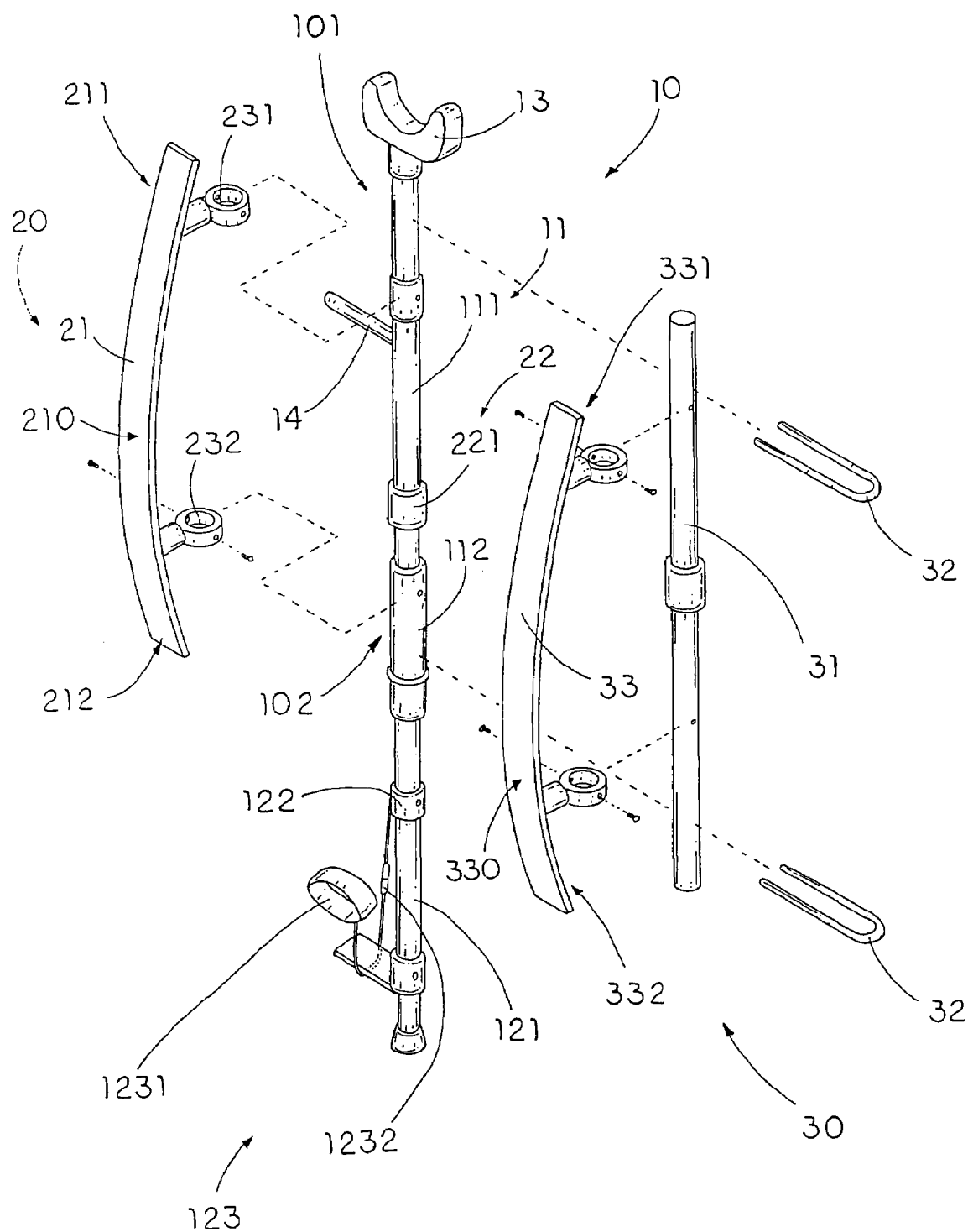
FIG. 2 is an exploded perspective view of the ambulatory hip fixation-traction splint frame according to the above first preferred embodiment of the present invention.
Figure 3:
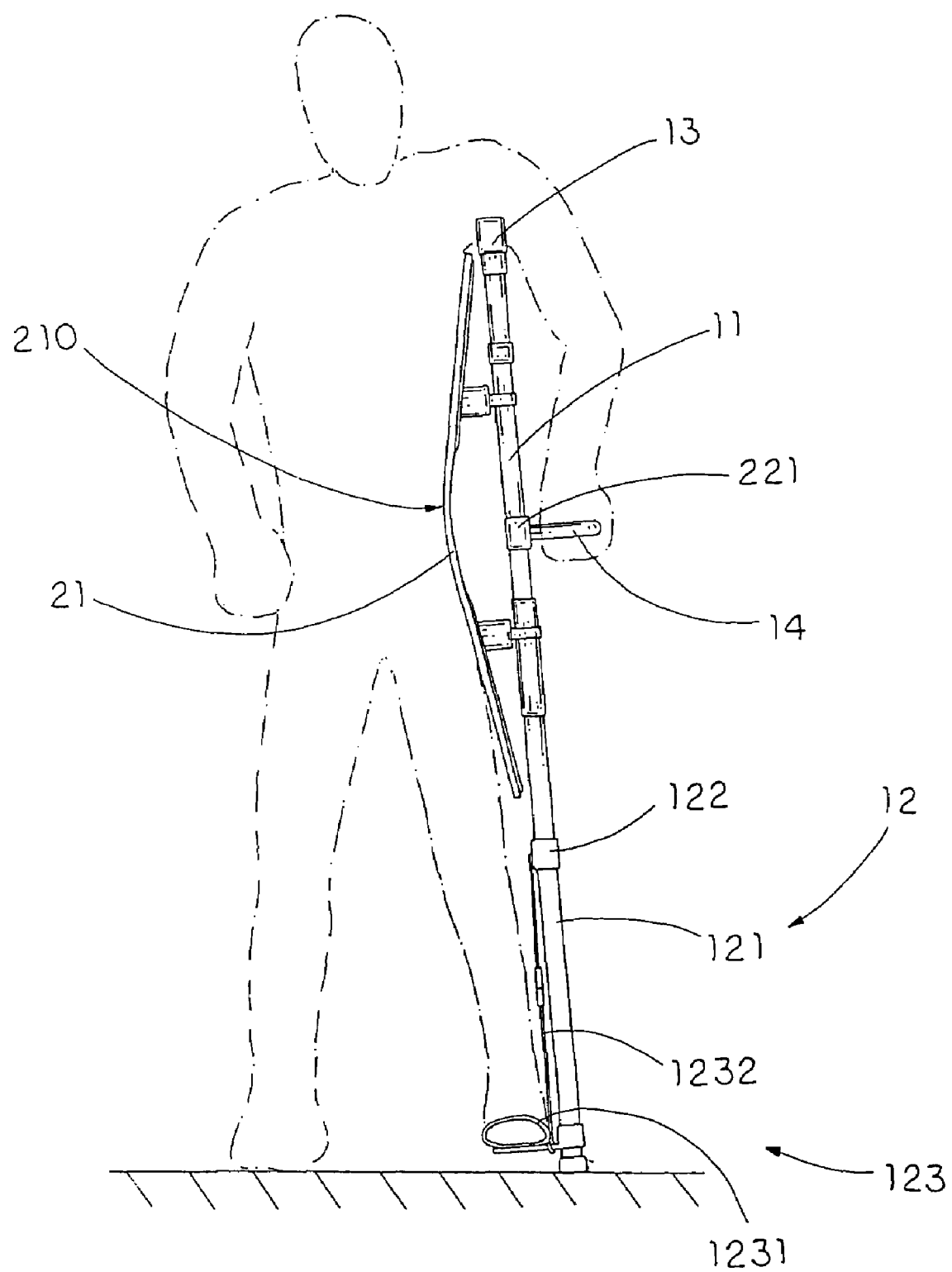
FIG. 3 is a front view of the ambulatory hip fixation-traction splint frame without front supporting splint according to the above first preferred embodiment of the present invention.

Referring to FIGS. 1 through 3 of the drawings, an ambulatory hip fixation-traction splint frame for a treated patient according to a preferred embodiment of the present invention is illustrated, wherein the ambulatory hip fixation-traction splint comprises is capable of retaining a treated patient having a fraction area at the side body thereof, such as rib fraction, waist fraction, or hip fraction, at a fixation position.

The ambulatory hip fixation-traction splint frame comprises a supporting frame 10 having an upper end 101 arranged for positioning below an armpit of the treated patient and a lower end 102 extending to position below a hip portion of the treated patient. The position below a hip portion includes a position below a heel.

The ambulatory hip fixation-traction splint frame further comprises a side splint assembly 20 comprising a flexible guiding frame 21 having first and second end portions 211, 212 mounted to the supporting frame 10 wherein the guiding frame 21 has a curved guiding surface 210 adapted for fixing on the side body of the treated patient to retain the side body thereof at a fixation position, and a curvature adjusting device 22 provided on the supporting frame 10 to adjustably retain a distance between the first and second end portions 211, 212 of the guiding frame 21 so as to selectively adjust a curvature of the guiding surface 210 with respect to the supporting frame 10 for fitting on the side body of the treated patient.

According to the preferred embodiment, the supporting frame 10 comprises an elongated body supporting member 11 having a length adapted for fittedly extending from the armpit of the treated patient to a hip portion, such as 2-3 cm below a heel, thereof to rigidly support an upper body of the patient without having a load on the treated leg. The body supporting member 11 is preferably made of rigid but light weight material such as metal in such a manner that when the treated patient incorporates with the ambulatory hip fixation-traction splint of the present invention, the body supporting member 11 of the supporting frame 10 functions as a body support to prevent any unwanted body movement, especially upper body and hip movements, of the treated patient.

The Ambulatory Hip Fixation-Traction Splint Frame is preferably made of rigid but light weight material, and suitable for X-ray examination, such as engineering plastic, in such a manner that when the treated patient incorporates with The Ambulatory Hip Fixation-Traction Splint Frame of the present invention, the body supporting member 11 of the supporting frame 10 functions as a body support, from armpit to whole leg, to prevent any unwanted body movement, to maintain hip fixation of the treated patient. At the same time, biomechanics fixation is rigid, light and handy, which has been able to replace and upgrade the traditional plaster splint immobilization.

The first end portion 211 of the guiding frame 21 is securely affixed to the body supporting member 11 below the upper end 101 thereof via a first frame joint 231 and the second end portion 212 of the guiding frame 21 is securely affixed to the body supporting member 11 above the lower end 102 thereof via a second frame joint 232 wherein the guiding surface 210 is provided between the first and second end portions 211, 212 of the guiding frame 21 and facing towards the side body of the treated patient. It is worth to mention that due to the flexibility of the guiding frame 21, the guiding frame 21 is capable of providing a retraction force on the guiding surface 210 against the side body of the treated patient so as to enhance the flexible body support, as a bio-mechanical support, of the present invention. Preferably, the guiding frame 21 is bent outwardly with respect supporting member 11 with a 20-30 degree, meanwhile, bent frontwardly with a degree 10-15 degree.

Figure 4:
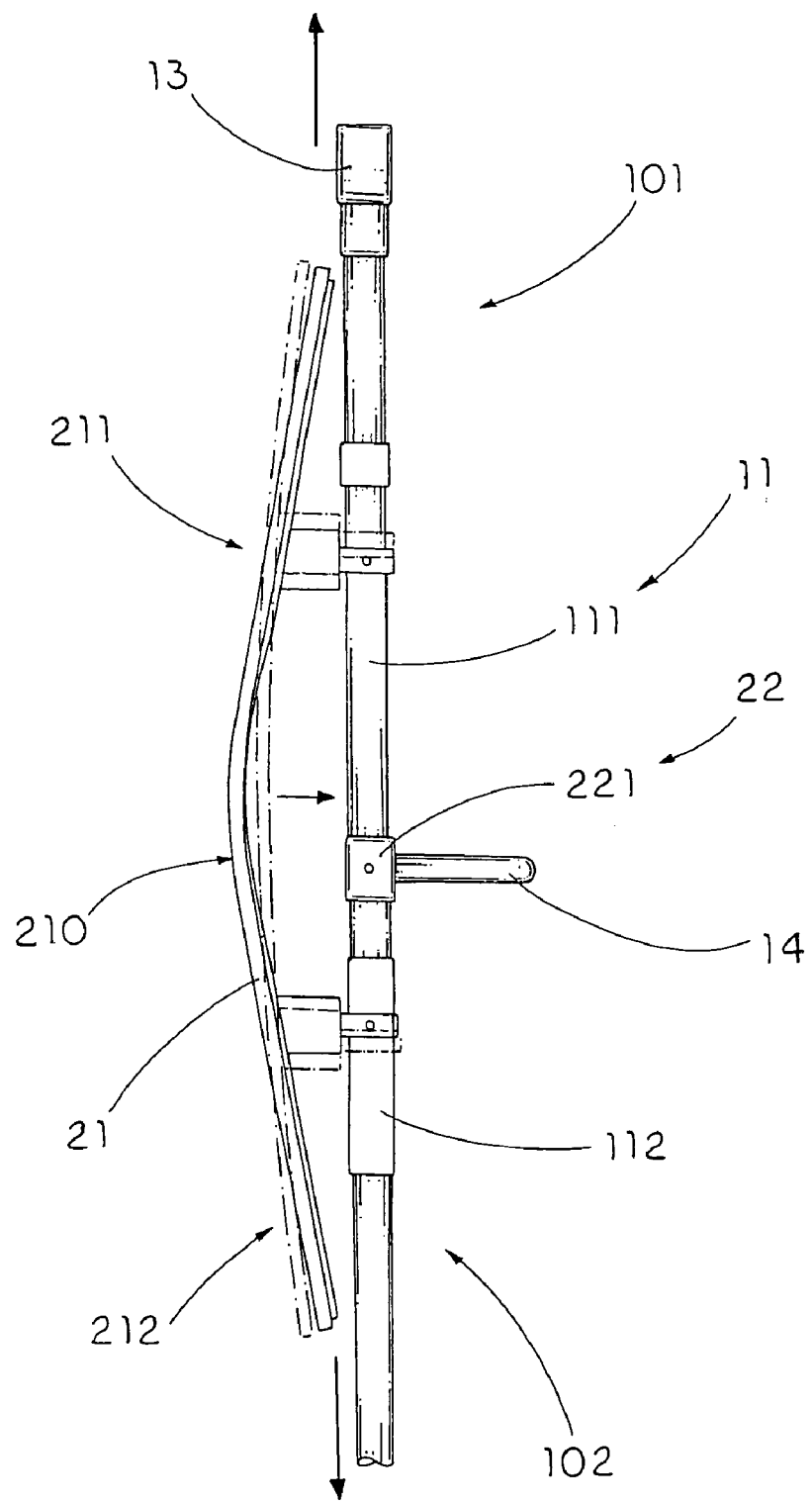
FIG. 4 is a side view of a curvature adjusting means of the ambulatory hip fixation-traction splint frame according to the above first preferred embodiment of the present invention.

As shown in FIG. 4, the body supporting member 11 comprises an upper tubular body 111 and a lower tubular body 112 slidably and coaxially mounted to the upper tubular body 111 in such a manner that when the upper tubular body 111 is slid away from the lower tubular body 112, the distance between the upper and lower ends 101, 102 of the body supporting member 11 is substantially increased, and when the upper tubular body 111 is slid towards to the lower tubular body 112, the distance between the upper and lower ends 101, 102 of the body supporting member 11 is substantially decreased. In other words, the length of the body supporting member 11 can be selectively adjusted to fit the body size of the treated patient.

The curvature adjusting device 22 comprises a frame locker 221 mounted on the body supporting member 11 to lock up the upper tubular body 111 with the lower tubular body 112 so as to securely retain the distance between the upper and lower ends 101, 102 of the body supporting member 11. Since the first and second end portions 211, 212 of the guiding frame 21 are securely affixed to the body supporting member 11 at two end portions thereof, the guiding frame 21 is bent more outwardly with respect to the body supporting member 11 while reducing the distance between the first and second end portions 211, 212 of the guiding frame 21 so as to increase the curvature of the guiding surface 210. Likewise, while increasing the distance between the first and second end portions 211, 212 of the guiding frame 21, the guiding frame 21 is bent less outwardly with respect to the body supporting member 11 so as to reduce the curvature of the guiding surface 210, as shown in FIG. 4.

Therefore, the frame locker 221 is capable of locking the upper tubular body 111 with the lower tubular body 112 to lock up the distance between the upper and lower ends 101, 102 of the body supporting member 11 so as to securely retain the curvature of the guiding surface 210. In other words, the curvature of the guiding surface 210 can be selectively adjusted by the position of the frame locker 221 along the body supporting member 11 for fitting the curvature of the side body of the treated patient.

Accordingly, the curvature of the guiding surface 210 of the guiding frame 21 is pre-adjusted to fit the side body of the treated patient. Therefore, the curvature of the treated patient, such as a fixation angle of a treated hip of the patient, should be pre-measured before placing the guiding frame 21 thereon. Also, the curvature of the guiding surface 210 of the guiding frame 21 should be locked to prevent the distortion of the guiding frame 21 after being used so as to affect the fixation treatment of the present invention.

Figure 5:
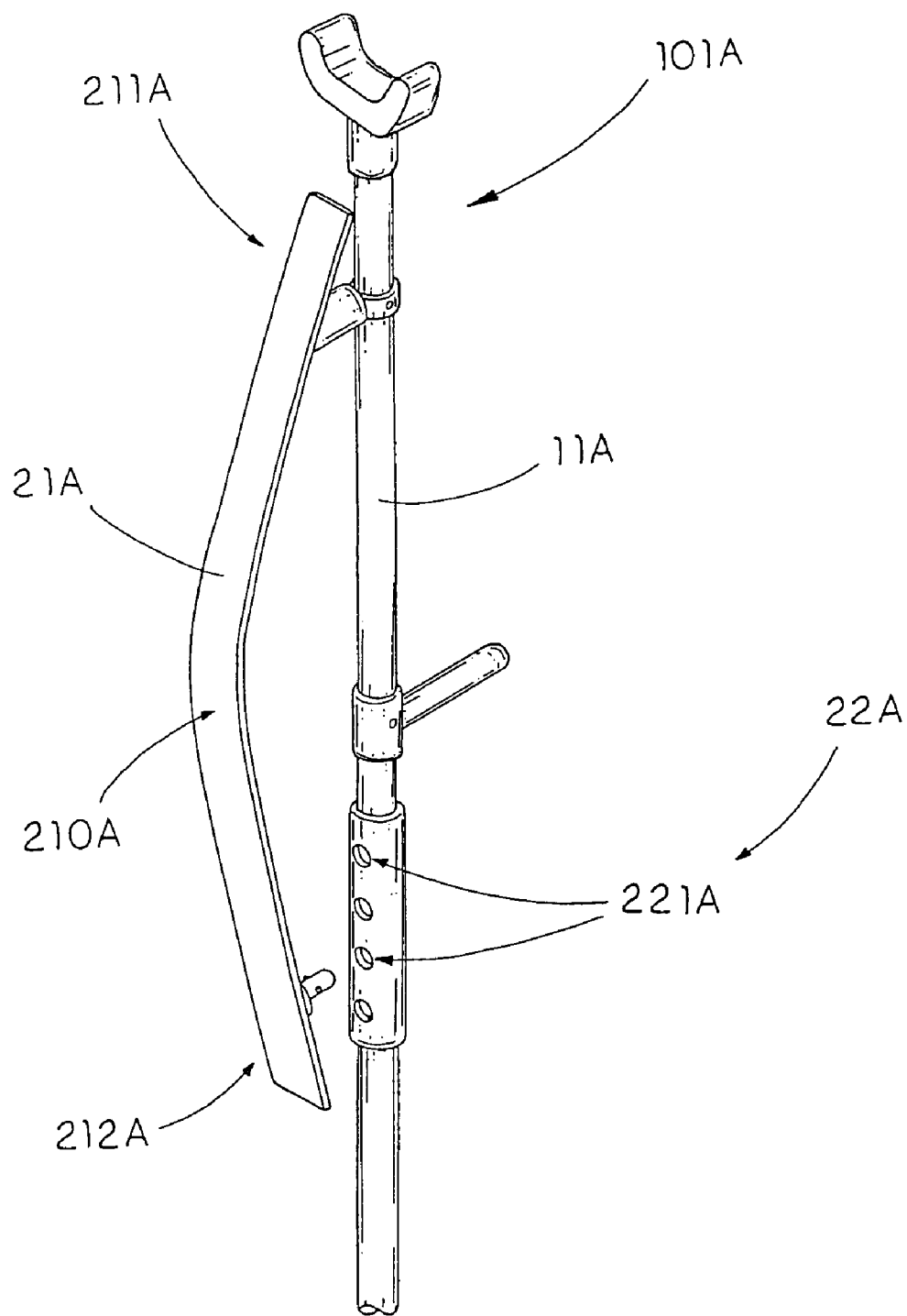
FIG. 5 illustrates an alternative mode of the curvature adjusting means of the ambulatory hip fixation-traction splint frame according to the above first preferred embodiment of the present invention.

FIG. 5 illustrates an alternative mode of the curvature adjusting device 22A which contains a plurality of engaging slots 221A spacedly provided on the body supporting member 11A wherein the first end portion 211A of the guiding frame 21A is securely affixed to the body supporting member 11A below the upper end 101A thereof and the second end portion 212A of the guiding frame 21A is selectively engaged with one of the engaging slots 221A so as to adjust the distance between the first and second end portions 211A, 212A of the guiding frame 21A and the curvature of the guiding surface 210A thereof.

In order to fix the guiding surface 210 on the side body of the treated patient, a bandage, or a fixation bandage system with elastic bandage, may be used to wrap around the upper body of the treated patient with the body supporting member 11, so that side body of the treated patient is substantially supported by the guiding frame 21 at the fixation position to prevent any unwanted movement of the upper body and the hip of the treated patient.

The supporting frame 10 further comprises a ground supporting member 12 comprising a ground stand 121 slidably and downwardly extended from the body supporting member 11 as a walking stick for distributing a weight of the treated patient to the ground, and a locking member 122 provided at the body supporting member 11 to lock up the body supporting member 11 with the ground supporting member 12 so as to selectively adjust a supportive portion of the ground stand 121 with respect to a height of the treated patient. In other words, the ground stand 121 is capable of adjustably extending from the body supporting member 11 to lengthen the supportive portion of the ground stand 121 for a taller treated patient and to shorten the supportive portion of the ground stand 121 for a shorter treated patient.

In addition, the supporting frame 10 further comprises an armpit resting support 13 mounted at the upper end 101 of the body supporting frame 11 for supporting the armpit of the treated patient so as to enhance the weight, especially the upper body, of the patient distributing to the ground through the ground stand 121. Moreover, a handgrip 14 is transversely extended from the body supporting frame 11 at a predetermined position for the treated patient so that the treated patient is able to hold the handgrip 14 to stabilize the body weight during movement.

The ground supporting member 12 further comprises a hip-stress releasing unit 123 which comprises a footstep retainer 1231 transversely extended from the ground stand 121 and means 1232 for applying a pulling force on the footstep retainer 1321 towards a ground end of the ground stand 121. The hip-stress releasing unit may be a foot continuous traction system.

Accordingly, the pulling means 1232 comprises a pulley system comprising an elongated element extended from the ground stand 121 to the footstep retainer 1231 through a pulley in such a manner that by selectively adjusting a length of the elongated element, the footstep retainer 1231 is slidably moved towards the ground end of the ground stand 121. In other words, when the treated patient is supported by the ground stand 121 while the foot of the treated patient is retained at the footstep retainer 1231, the pulling means 1232 substantially applies a pulling force, such as in a range between 0 kg and 10 kg, to slightly pull the foot of the treated patient downwardly with respect to the hip portion thereof, so as to minimize the stress around the hip portion of the treated patient. Therefore, the hip-stress releasing unit 123 is capable of providing a cushion effect and absorbing a reaction force at the hip portion of the treated patient, so as to reduce the pressure against on the fraction area of the treated patient.

It is worth to mention that when the treated patient has a waist or hip fraction, the treated patient is unable to stand or walk since the leg of the treated patient is not strong enough and is too weak to support the weight thereof while highly increasing the pressure on the fraction area through the foot on the ground. Therefore, the leg of the treated patient is capable of being supported by the footstep retainer 1231 to minimize the stress on the fraction area through the leg during movement. It is worth to mention that a distance between the armpit resting support 13 and the ground end of the ground stand 121 should be adjusted, such as in a range of 2 to 3 cm, as a distance between the armpit of the treated patient with respect to the ground in order to optimize the body weight support of the present invention. Furthermore, the hip joint is controlled by biomechanics, thereby guaranteeing the flexion, rotation and extension of hip joint could be cooperatively functioned.

As shown in FIG. 2, the ambulatory hip fixation-traction splint frame further comprises a front splint assembly 30 comprising a side supporting member 31, a side extension frame 32 transversely extended from the body supporting member 11 to securely connect to the side supporting member 31, and a flexible front guiding frame 33 having first and second end portions 331, 332 spacedly mounted to the side supporting member 31 and a curved front guiding surface 330 adapted for fixing on a front body of the treated patient to retain the front body thereof at a fixation position, as shown in FIG. 1. In other words, the side body and the front side body of the patient are substantially supported by the guiding frame 21 and the front guiding frame 33 respectively to prevent any unwanted movement of the treated patient, as shown in FIG. 1.

Accordingly, the dimension of the front splint assembly 30 is pre-measured for the user according to the size of the user's body such that the angle and distance between the front guiding frame 33 and the guiding frame 21 is preadjusted by the position of the side supporting member 31 through the side extension frame 32. Therefore, the broken or fracture part of the patient must be immobilized in a predetermined position so as to eliminate the risk of bone displacement or even distortion.

Accordingly, the front guiding frame 33 is constructed as the guiding frame 21 that is capable of adjusting a curvature of the front guiding surface 331 for fittedly fixing on the front body of the treated patient, i.e. the side portion of the chest, including a front portion of the chest, abdomen and thigh, of the treated patient. Moreover, the front guiding frame 33 is capable of being rotated with respect to the body supporting member 11 through the side supporting member 32 to adjust the position of the front guiding surface 330 facing towards the front body of the treated patient.

The treated patient may have a tendency to lean his or her upper body forward wherein the forward leaning movement of the treated patient may hurt the fraction area thereof. Therefore, when the front body of the treated patient is supported by the front splint assembly 30, the upper body of the treated patient is retained in a fixation position, that is to say, the upper body movement of the treated patient could be acclimated with his hip retained in a good fixation position, so as to prevent any pressure applying on the fraction area of the treated patient and to prevent any harmful hip movement.

Figure 6:
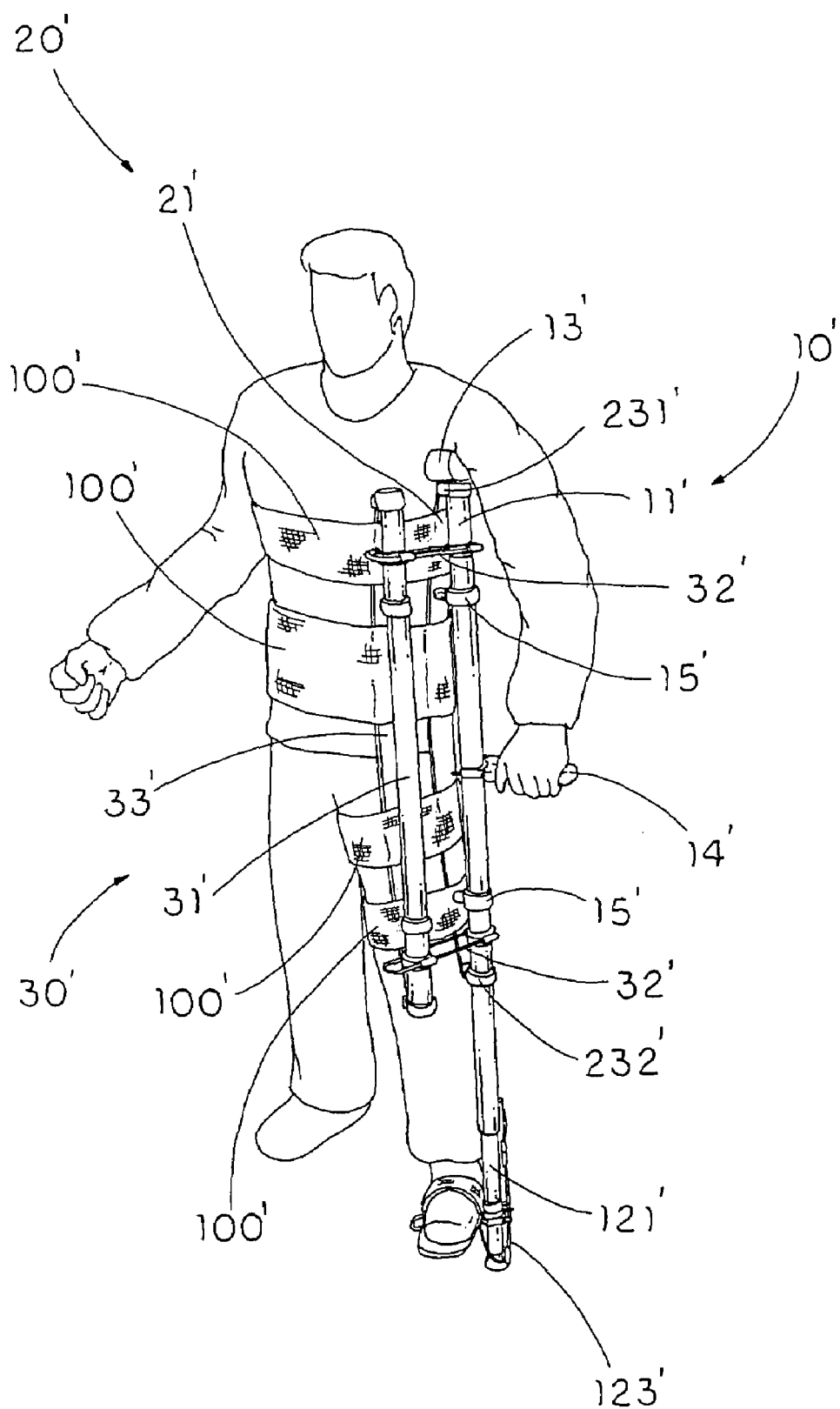
FIG. 6 is a perspective view of an ambulatory hip fixation-traction splint frame for a treated patient according to a second preferred embodiment of the present invention.

As shown in FIG. 6, an ambulatory hip fixation-traction splint frame of a second embodiment illustrates an alternative mode of the first embodiment of the present invention.

According to the second embodiment, the ambulatory hip fixation-traction splint frame comprises a supporting frame 10' having an upper end 101' arranged for positioning below an armpit of the treated patient and a lower end 102' arranged for positioning below a hip portion of the treated patient. The ambulatory hip fixation-traction splint frame further comprises a side splint assembly 20' which comprises a flexible guiding frame 21' and two coupling joints 231', 232'.

The guiding frame 21' has first and second end portions 211', 212', and a curved guiding surface 210', having a predetermined curvature, defining between the first and second end portions 211', 212' for biasing against a side body of the treated patient.

The coupling joints 231', 232' are adjustably mounted on the supporting frame 10' to connect with the first and second end portions 211', 212' of the guiding frame 21' respectively so as to retain the curvature of the guiding surface 210 of the guiding frame 20' for fitting on the side body of the treated patient.

According to the preferred embodiment, the supporting frame 10' comprises an elongated body supporting member 11' having a length adapted for fittingly extending from the armpit of the treated patient to the hip portion or to 2-3 cm below his heel thereof to rigidly support an upper body of the treated patient without an additional load on the treated leg. The body supporting member 11' is preferably made of rigid but lightweight material such as metal in such a manner that when the treated patient employs with the ambulatory hip fixation-traction splint of the present invention, the body supporting member 11' of the supporting frame 10' functions as a body support to prevent any unwanted body movement, especially upper body and hip movements, of the treated patient.

On the other hand, the ambulatory hip fixation-traction splint frame of the present invention is preferably made of rigid but light weight material, and suitable for X-ray examination, such as engineering plastic, in such a manner that when the treated patient incorporates with the ambulatory hip fixation-traction splint frame of the present invention, the body supporting member 11' of the supporting frame 10' functions as a body support, from armpit to whole leg, to prevent any unwanted body movement, to maintain hip fixation of the treated patient.

The first end portion 211' of the guiding frame 21' is securely affixed to the supporting member 11 below the upper end 101' thereof via one of the coupling joints 231' and the second end portion 212' of the guiding frame 21' is securely affixed to the body supporting member 11' above the lower end 102' thereof via another coupling joint 232', wherein the guiding surface 210' is provided between the first and second end portions 211', 212' of the guiding frame 21' and facing towards the side body of the treated patient. It is worth to mention that due to the flexibility of the guiding frame 21', the guiding frame 21' is capable of providing a retraction force, such as an elastic fixation force, on the guiding surface 201' against the side body of the treated patient so as to enhance the flexible body support of the present invention.

Each of the coupling joints 231', 232' is slidably connected to the body supporting member 11' of the supporting frame 10 between the upper and lower ends 101', 102' thereof wherein the coupling joints 231', 232' are arranged to be spacedly locked up on the supporting frame 10' via locking elements such as screws or bolts.

Figure 7:
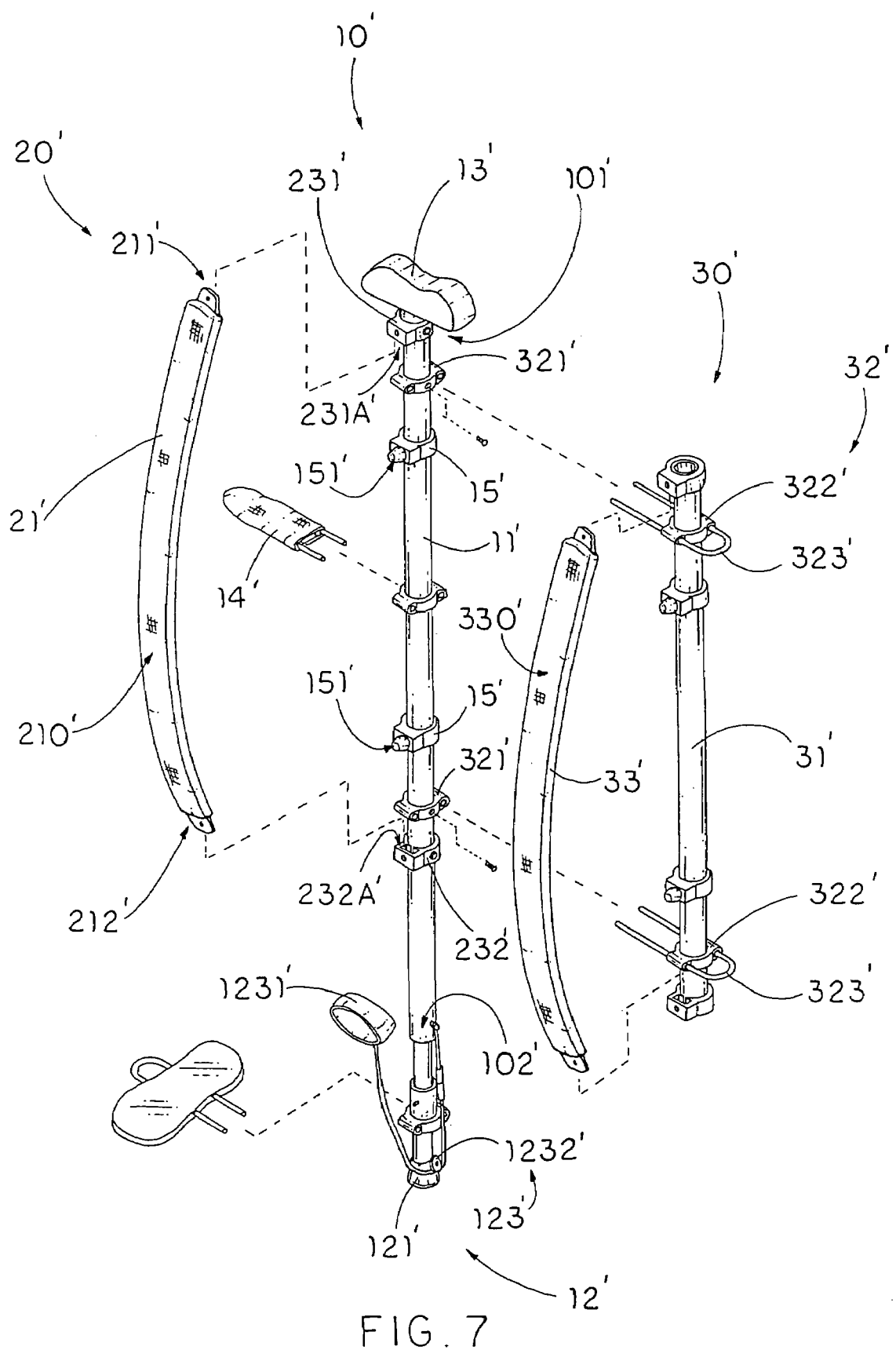
FIG. 7 is an exploded perspective view of the ambulatory hip fixation-traction splint frame according to the above second preferred embodiment of the present invention.

As shown in FIG. 7, each of the coupling joints 231', 232' has a holding slot 231A', 232A' provided thereon wherein the first and second end portions 211', 212' of the guiding frame 21' are respectively inserted into the holding slots 231A', 232A' of the coupling joints 231', 232' so as to mount the guiding frame 21' to the body supporting member 11' of the supporting frame 10'. It is worth to mention that by adjustably mounting the coupling joints 231', 232' on the body supporting member 11' of the supporting frame 10', the curvature of the guiding surface 210' of the guiding frame 20' can be selectively adjusted by a distance between the two coupling joints 231', 232'. Therefore, by reducing the distance between the two coupling joints 231', 232', the guiding frame 21' is bent more outwardly with respect to the body supporting member 11' to substantially increase the curvature of guiding surface 210' of the guiding frame 21'. In other words, the curvature of the guiding surface 210' of the guiding frame 21' will be reduced by increasing the distance between the two coupling joints 231', 232'.

Figure 8:
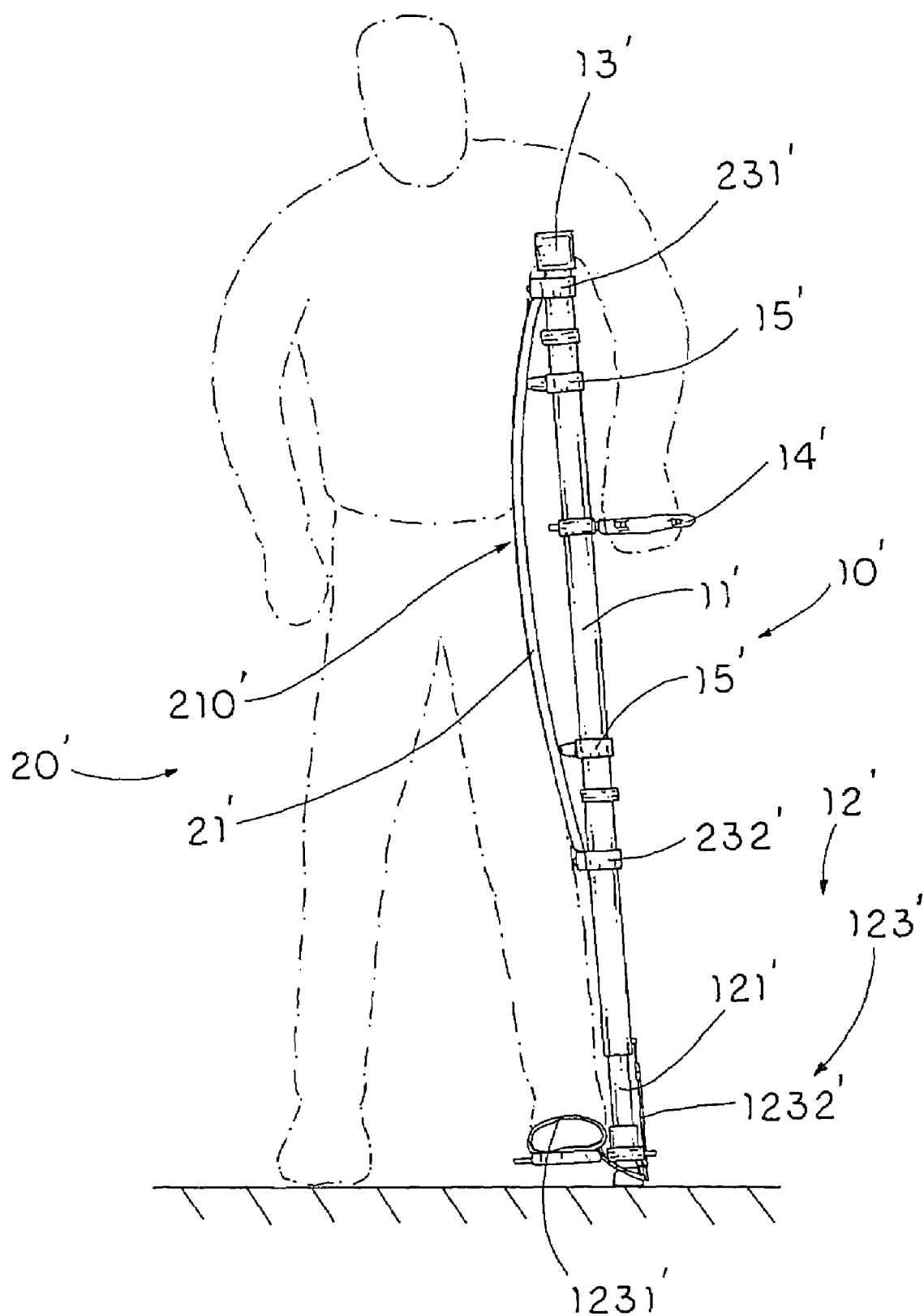
FIG. 8 is a front view of the ambulatory hip fixation-traction splint frame without a front splint assembly according to the above second preferred embodiment of the present invention.

Therefore, when the two coupling joints 231', 232' are locked up on the body supporting member 11' of the supporting frame 10' so as to lock up the distance between the two coupling joints 231', 232', the first and second end portions 211', 212' of the guiding frame 20' are respectively inserted into the holding slots 231A', 232A' of the coupling joints 231', 232', so as to securely retain the curvature of the guiding surface 210' of the guiding frame 21' for fitting on the side body of the treated patient, as shown in FIG. 8. Accordingly, the curvature of the guiding surface 210' of the guiding frame 21' is pre-adjusted to fit the side body of the treated patient. Therefore, the curvature of the treated patient should be pre-measured before placing the guiding frame 21' thereon. Also, the curvature of the guiding surface 210' of the guiding frame 21' should be locked to prevent the distortion of the guiding frame 21' after being used so as to affect the fixation treatment of the present invention.

As shown in FIG. 7, the side splint assembly 20' further comprises at least a curvature retainer 15' mounted on the body supporting member 11' wherein the curvature retainer 15' has a supporting end 151' extending to bias against the guiding frame 21' to retain the curvature of the guiding surface 210' of the guiding frame 21'. In order to fix the guiding surface 210' on the side body of the treated patient, a fabric wrap, such as an elastic bandage 100', is used to wrap around the upper body of the treated patient with the guiding frame 21', as shown in FIG. 6, so that the side body of the treated patient is substantially supported by the guiding frame at the fixation position to prevent any unwanted movement of the upper body of the treated patient.

The supporting frame 10' further comprises a ground supporting member 12' comprising a ground stand 121' adjustably and downwardly extended from the body supporting member 11' as a walking stick for distributing a weight of the treated patient to the ground. Accordingly, the ground stand 121' is slidably extended from the body supporting member 11' to selectively adjust a supporting portion of the ground stand 121' with respect to a height of the treated patient. In other words, the ground stand 121' is capable of adjustably extending from the body supporting member 11' to lengthen the supporting portion of the ground stand 121' for a taller treated patient and to shorten the supporting portion of the ground stand 121' for a shorter treated patient. Once the ground stand 121' is downwardly slid from the body supporting member 11' to fit the height of the treated patient, the ground stand 121' can be locked up from the body supporting member 11 via a conventional locking element such as screw or bolt.

In addition, the supporting frame 10' further comprises an armpit resting support 13' mounted at the upper end 101' of the body supporting member 11' for supporting the armpit of the treated patient so as to enhance the weight, especially the upper body of the patient, distributing to the ground through the ground stand 121'. Moreover, a handgrip 14' is transversely extended from the body supporting member 11' at a predetermined position for the treated patient so that the treated patient is able to hold the handgrip 14' to stabilize the body weight during movement, as shown in FIG. 8.

The ground supporting member 12' further comprises a hip-stress releasing unit 123' which comprises a footstep retainer 1231' transversely extended from the ground stand 121' and means 1232' for applying a traction pulling force on the footstep retainer 1321' towards a ground end of the ground stand 121'.

Accordingly, the pulling means 1232' comprises a pulley system comprising an elongated element extended from the ground stand 121' to the footstep retainer 1231' through a pulley in such a manner that by selectively adjusting a length of the elongated element, the footstep retainer 1231' is slidably moved towards the ground end of the ground stand 121'. In other words, when the treated patient is supported by the ground stand 121' while the foot of the treated patient is retained at the footstep retainer 1231', the pulling means 1232' substantially applies a traction pulling force to slightly pull the foot of the treated patient downwardly with respect to the hip portion thereof, so as to minimize the stress around the hip portion of the treated patient. Therefore, the hip-stress releasing unit 123' is capable of providing a cushion effect and absorbing a reaction force at the hip portion of the treated patient, so as to reduce the pressure against on the fraction area of the treated patient.

As shown in FIG. 7, the ambulatory hip fixation-traction splint frame further comprises a front splint assembly 30' comprising a side supporting member 31', a side extension frame 32' transversely extended from the body supporting member 11' to securely connect to the side supporting member 31', and a flexible front guiding frame 33', which is mounted to the side extension frame 32', having a curved front guiding surface 330' adapted for biasing on a front body of the treated patient to retain the front body thereof at a fixation position, as shown in FIG. 6. In other words, the side body and the front side body of the patient are substantially supported by the guiding frame 21' and the front guiding frame 33' respectively to prevent any unwanted movement of the treated patient, as shown in FIG. 6.

As shown in FIG. 7, the side supporting member 31' is constructed as the body supporting member 11' and the front guiding member 33 is constructed as the guiding member 21', wherein two ends of the front guiding member 33' are affixed to the side supporting member 31' to retain a curvature of the front guiding surface 330' of the front guiding member 33'.

The side extension frame 32' comprises two pairs of first and second frame joints 321', 322' adjustably mounted on the body supporting member 11' and the side supporting member 31' respectively and two extension arms 323' slidably connecting the first frames joints 321' with the second frame joints 322' respectively, so as to substantially connect the side supporting member 31' with the body supporting member 11'.

According to the preferred embodiment, each of the first frame joints 321', having a first connecting slot, is rotatably and spacedly connected to the body supporting member 11' and each of the second frame joints 322', having a second connecting slot, is connected to the side supporting member 31' to align with the respective first frame joint 321', wherein each of the extension arms 323' is slidably inserted into the first connecting slot of the respective first frame joint 321' through the second connecting slot of the respective second frame joint 322' in such a manner that the side supporting member 31' is sidewardly extended from the body supporting member 11' via the extension arms 323' so as to support the front guiding frame 33' for biasing against the front body of the treated patient.

In order to fit the front guiding surface 330' of the front guiding frame 33' to bias against the front body of the treated patient, the first frame joints 321' are arranged to rotate about the body supporting member 11' to fold the side supporting member 31 towards the treated patient at a position that the front guiding surface 330' of the front guiding frame 33' is rested on the front side of the treated patient. Therefore, the first frame joints 321' are then locked up at the body supporting member 11' via conventional locking elements, such as screws or bolts, so as to retain the front guiding surface 330 of the front guiding frame 33' in position to support the front side of the treated patient.

As shown in FIG. 7, each of the extension arms 323', having a U-shaped, has two parallel inserting arms slidably inserting into two first connecting slots of the respective first frame joint 321' through two second connecting slots of the respective second frame joint 322'. In other words, a distance between the body supporting member 11' and the side supporting member 31' can be selectively adjusted by sliding the side supporting member 31' along the extension arms 323' so as to adjust the front guiding frame 33' to fittingly bias against the front side of the treated patient.

It is worth to mention that in order to fix the guiding surface 210' and the front guiding surface 330' on the body of the treated patient, the elastic bandage 100' is used to wrap around the upper body, the waist, and the leg of the treated patient with the body supporting member 11' and the front guiding frame 33', so that body of the treated patient is substantially supported by the ambulatory hip fixation-traction splint frame at the fixation position to prevent any unwanted movement of the body of the treated patient.

Conclusively, the ambulatory hip fixation-traction splint frame enable the patients rotate his joints, move, stand, and walk without bearing any load. In short, the present invention breaks through the limitation of conventional rest cure treatment, provides patients of hip area fracture huge convenience.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure form such principles. Therefore, this invention includes all modifications encompassed within the spirit and scope of the following claims.

What is claimed is:

1. The ambulatory hip fixation-traction splint frame for a treated patient, comprising:
   a supporting frame comprising an elongated body supporting member having an upper end arranged for positioning below an armpit of said treated patient and a lower end arranged for positioning below a hip portion of said treated patient; and
   a side splint assembly, comprising:
   a flexible guiding frame having first and second end portions, and a curved guiding surface, having a predetermined curvature, defining between said first and second ends for biasing against a side body of said treated patient; and
   two coupling joints adjustably mounted on said supporting frame to connect with said first and second end portions of said guiding frame respectively so as to retain said curvature of said guiding surface of said guiding frame for fitting on said side body of said treated patient, wherein each of said coupling joints has a holding slot provided thereon, wherein said first and second end portions of said guiding frame are respectively inserted into said holding slots of said coupling joints so as to mount said guiding frame to said body supporting member of said supporting frame.

2. The ambulatory hip fixation-traction splint frame, as recited in claim 1, wherein said side splint assembly further comprises at least a curvature retainer mounted on said body supporting member, wherein said curvature retainer has a supporting end extending to bias against said guiding frame to retain said curvature of said guiding surface of said guiding frame.

3. The ambulatory hip fixation-traction splint frame, as recited in claim 2, wherein said supporting frame further comprises a ground supporting member which comprises a ground stand adjustably and downwardly extended from said body supporting member as a walking stick for distributing a weight of said treated patient to through said ground stand.

4. The ambulatory hip fixation-traction splint frame, as recited in claim 3, wherein said ground supporting member further comprises a hip-stress releasing unit which comprises a footstep retainer transversely extended from said ground stand and means for applying a traction pulling force on said footstep retainer towards a ground end of said ground stand.

5. The ambulatory hip fixation-traction splint frame, as recited in claim 4, further comprising a front splint assembly which comprises a side supporting member, a side extension frame transversely extended from said body supporting member to securely connect to said side supporting member, and a flexible front guiding frame, which is mounted to said side extension frame, having a curved front guiding surface adapted for biasing on a front body of said treated patient to retain said front body thereof at a fixation position.

6. The ambulatory hip fixation-traction splint frame, as recited in claim 5, wherein said side extension frame comprises two pairs of first and second frame joints adjustably mounted on said body supporting member and said side supporting member respectively and two extension arms slidably connecting said first frames joints with said second frame joints respectively to substantially connect said side supporting member with the body supporting member so as to adjust said front guiding surface of said front guiding member for biasing against said front side of said treated patient.

7. The ambulatory hip fixation-traction splint frame, as recited in claim 6, wherein said supporting frame further comprises an armpit resting support mounted at said upper end of said body supporting member for supporting said armpit of said treated patient thereon, and a handgrip is transversely extended from said body supporting member.

8. The ambulatory hip fixation-traction splint frame, as recited in claim 7, wherein said guiding surface and said front guiding surface are arranged for affixing on said body of said treated patient by wrapping at least an elastic bandage around said upper body, waist, and leg of said treated patient with said body supporting member and said front guiding frame.

9. The ambulatory hip fixation-traction splint frame, as recited in claim 6, wherein said guiding surface and said front guiding surface are arranged for affixing on said body of said treated patient by wrapping at least an elastic bandage around said upper body, waist, and leg of said treated patient with said body supporting member and said front guiding frame.

10. The ambulatory hip fixation-traction splint frame, as recited in claim 5, wherein said guiding surface and said front guiding surface are arranged for affixing on said body of said treated patient by wrapping at least an elastic bandage around said upper body, waist, and leg of said treated patient with said body supporting member and said front guiding frame.

11. The ambulatory hip fixation-traction splint frame, as recited in claim 4, wherein said supporting frame further comprises an armpit resting support mounted at said upper end of said body supporting member for supporting said armpit of said treated patient thereon, and a handgrip is transversely extended from said body supporting member.

12. The ambulatory hip fixation-traction splint frame, as recited in claim 3, further comprising a front splint assembly which comprises a side supporting member, a side extension frame transversely extended from said body supporting member to securely connect to said side supporting member, and a flexible front guiding frame, which is mounted to said side extension frame, having a curved front guiding surface adapted for biasing on a front body of said treated patient to retain said front body thereof at a fixation position.

13. The ambulatory hip fixation-traction splint frame, as recited in claim 12, wherein said side extension frame comprises two pairs of first and second frame joints adjustably mounted on said body supporting member and said side supporting member respectively and two extension arms slidably connecting said first frames joints with said second frame joints respectively to substantially connect said side supporting member with the body supporting member so as to adjust said front guiding surface of said front guiding member for biasing against said front side of said treated patient.

14. The ambulatory hip fixation-traction splint frame, as recited in claim 2, wherein said supporting frame further comprises an armpit resting support mounted at said upper end of said body supporting member for supporting said armpit of said treated patient thereon, and a handgrip is transversely extended from said body supporting member.

15. The ambulatory hip fixation-traction splint frame, as recited in claim 1, wherein said supporting frame further comprises a ground supporting member which comprises a ground stand adjustably and downwardly extended from said body supporting member as a walking stick for distributing a weight of said treated patient to through said ground stand.

16. The ambulatory hip fixation-traction splint frame, as recited in claim 15, wherein said ground supporting member further comprises a hip-stress releasing unit which comprises a footstep retainer transversely extended from said ground stand and means for applying a traction pulling force on said footstep retainer towards a ground end of said ground stand.

17. The ambulatory hip fixation-traction splint frame, as recited in claim 1, further comprising a front splint assembly which comprises a side supporting member, a side extension frame transversely extended from said body supporting member to securely connect to said side supporting member, and a flexible front guiding frame, which is mounted to said side extension frame, having a curved front guiding surface adapted for biasing on a front body of said treated patient to retain said front body thereof at a fixation position.

18. The ambulatory hip fixation-traction splint frame, as recited in claim 17, wherein said side extension frame comprises two pairs of first and second frame joints adjustably mounted on said body supporting member and said side supporting member respectively and two extension arms slidably connecting said first frames joints with said second frame joints respectively to substantially connect said side supporting member with the body supporting member so as to adjust said front guiding surface of said front guiding member for biasing against said front side of said treated patient.

19. The ambulatory hip fixation-traction splint frame for a treated patient, comprising:
  a supporting frame comprising an elongated body supporting member having an upper end arranged for positioning below an armpit of said treated patient and a lower end arranged for positioning below a hip portion of said treated patient; and
  a side splint assembly, comprising:
  a flexible guiding frame having first and second end portions, and a curved guiding surface, having a predetermined curvature, defining between said first and second ends for biasing against a side body of said treated patient; and
  two coupling joints adjustably mounted on said supporting frame to connect with said first and second end portions of said guiding frame respectively so as to retain said curvature of said guiding surface of said guiding frame for fitting on said side body of said treated patient, wherein said supporting frame further comprises a ground supporting member which comprises a ground stand adjustably and downwardly extended from said body supporting member as a walking stick for distributing a weight of said treated patient to through said ground stand.

20. The ambulatory hip fixation-traction splint frame as recited in claim 19, wherein said ground supporting member further comprises a hip-stress releasing unit which comprises a footstep retainer transversely extended from said ground stand and means for applying a traction pulling force on said footstep retainer towards a ground end of said ground stand.

21. The ambulatory hip fixation-traction splint frame for a treated patient, comprising:
  a supporting frame comprising an elongated body supporting member having an upper end arranged for positioning below an armpit of said treated patient and a lower end arranged for positioning below a hip portion of said treated patient; and
  a side splint assembly, comprising:
  a flexible guiding frame having first and second end portions, and a curved guiding surface, having a predetermined curvature, defining between said first and second ends for biasing against a side body of said treated patient; and
  two coupling joints adjustably mounted on said supporting frame to connect with said first and second end portions of said guiding frame respectively so as to retain said curvature of said guiding surface of said guiding frame for fitting on said side body of said treated patient; and
  a front splint assembly which comprises a side supporting member, a side extension frame transversely extended from said body supporting member to securely connect to said side supporting member, and a flexible front guiding frame, which is mounted to said side extension frame, having a curved front guiding surface adapted for biasing on a front body of said treated patient to retain said front body thereof at a fixation position.

22. The ambulatory hip fixation-traction splint frame, as recited in claim 21, wherein said side extension frame comprises two pairs of first and second frame joints adjustably mounted on said body supporting member and said side supporting member respectively and two extension arms slidably connecting said first frames joints with said second frame joints respectively to substantially connect said side supporting member with the body supporting member so as to adjust said front guiding surface of said front guiding member for biasing against said front side of said treated patient.

23. An ambulatory hip fixation-traction splint frame for a treated patient, comprising:
- a supporting frame comprising an elongated body supporting member having an upper end arranged for positioning below an armpit of said treated patient and a lower end arranged for positioning below a hip portion of said treated patient;
- a side splint assembly, comprising:
- a flexible guiding frame having first and second end portions, and a curved guiding surface, having a predetermined curvature, defining between said first and second ends for biasing against a side body of said treated patient; and
- two coupling joints adjustably mounted on said supporting frame to connect with said first and second end portions of said guiding frame respectively so as to retain said curvature of said guiding surface of said guiding frame for fitting on said side body of said treated patient;

- a ground supporting member which comprises a ground stand adjustably and downwardly extended from said body supporting member as a walking stick for distributing a weight of said treated patient to through said ground stand; and

- a front splint assembly which comprises a side supporting member, a side extension frame transversely extended from said body supporting member to securely connect to said side supporting member, and a flexible front guiding frame, which is mounted to said side extension frame, having a curved front guiding surface adapted for biasing on a front body of said treated patient to retain said front body thereof at a fixation position.

* * * * *